(12) United States Patent
Paradise et al.

(10) Patent No.: US 9,669,140 B2
(45) Date of Patent: Jun. 6, 2017

(54) DRYING RACK

(71) Applicant: Helen of Troy Limited, Belleville, St. Michael (BB)

(72) Inventors: Charles Paradise, Brooklyn, NY (US); Shelley Palazzolo, Brooklyn, NY (US); Troy Phipps, Brooklyn, NY (US)

(73) Assignee: Helen of Troy Limited, Belleville, St. Michael (BB)

(*) Notice: Subject to any disclaimer, the term of this patent is extended or adjusted under 35 U.S.C. 154(b) by 44 days.

(21) Appl. No.: 14/883,005

(22) Filed: Oct. 14, 2015

(65) Prior Publication Data
US 2017/0065079 A1    Mar. 9, 2017

Related U.S. Application Data

(60) Provisional application No. 62/215,213, filed on Sep. 8, 2015.

(51) Int. Cl.
*A61M 1/06*    (2006.01)
(52) U.S. Cl.
CPC .................. *A61M 1/062* (2014.02)
(58) Field of Classification Search
CPC .... B65D 25/10; B65D 25/106; B65D 25/108; A47B 81/007; A47B 81/02; A47B 81/04
USPC ... 211/41.3, 41.4, 41.5, 41.6, 69, 69.5, 69.6, 211/69.7, 70.6; 206/361, 362, 366, 369, 206/372, 373, 378, 379
See application file for complete search history.

(56) References Cited

U.S. PATENT DOCUMENTS

| | | | |
|---|---|---|---|
| 4,955,478 A * | 9/1990 | Rau .................. | B25H 3/003 16/221 |
| 6,170,120 B1 | 1/2001 | Lu | |
| 6,321,416 B1 | 11/2001 | Lu | |
| 6,398,027 B1 | 6/2002 | Ryu | |
| 6,547,074 B1 * | 4/2003 | Chen .................. | B25H 3/003 206/379 |
| 7,096,534 B2 | 8/2006 | Wang et al. | |
| 7,100,244 B2 | 9/2006 | Qin et al. | |
| 7,270,235 B2 * | 9/2007 | Chen .................. | B25H 3/003 206/349 |
| 7,328,797 B2 * | 2/2008 | Lin ..................... | A45F 5/02 206/372 |
| 7,386,330 B2 | 6/2008 | Takagi | |
| 7,428,970 B2 * | 9/2008 | Chen .................. | B25H 3/003 206/372 |
| 7,513,468 B2 | 4/2009 | Jung et al. | |
| 7,584,525 B2 | 9/2009 | Chern | |
| 7,912,523 B2 | 3/2011 | Anand et al. | |

(Continued)

OTHER PUBLICATIONS

International Search Report filed in PCT/US16/43039 mailed Oct. 14, 2016.

*Primary Examiner* — Joshua Rodden
(74) *Attorney, Agent, or Firm* — Rankin, Hill & Clark LLP

(57) ABSTRACT

A drying rack includes a first rack, a second rack and a movable core member. The second rack is pivotally connected with the first rack. The movable core member includes a receptacle configured to receive an associated cleaning device. The movable core member is operatively connected for pivotal movement with and pivotal movement with respect to each rack so as to change a relative location of the receptacle with respect to at least one of the first rack and the second rack based on a relative position of the first rack with respect to the second rack.

13 Claims, 11 Drawing Sheets

(56) References Cited

U.S. PATENT DOCUMENTS

| | | | |
|---|---|---|---|
| D673,366 S | 1/2013 | Schumann | |
| D761,513 S | 7/2016 | Traub | |
| 2002/0092786 A1* | 7/2002 | Shu | B25H 3/003 206/379 |
| 2005/0056559 A1* | 3/2005 | Chen | B25H 3/003 206/372 |
| 2005/0161356 A1* | 7/2005 | Chen | B25H 3/003 206/373 |
| 2006/0037878 A1 | 2/2006 | Brown | |
| 2006/0201837 A1* | 9/2006 | Lin | B25H 3/003 206/379 |
| 2008/0308509 A1* | 12/2008 | Giuseppe | A47L 19/04 211/41.3 |
| 2010/0269296 A1 | 10/2010 | Lin | |
| 2011/0047754 A1 | 3/2011 | Takahashi | |

* cited by examiner

DRYING RACK

BACKGROUND

The present disclosure relates to a drying rack including associated cleaning brushes that can be used to clean and subsequently dry items such as parts of a breast pump. A breast pump is a device used by mothers for expressing their breast milk into a baby feeding bottle. The breast pump includes various parts which typically require cleaning after use, such as a breast receiving cup or funnel.

BRIEF DESCRIPTION

A drying rack includes a first rack, a second rack and a movable core member. The second rack is pivotally connected with the first rack. The movable core member includes a receptacle configured to receive an associated cleaning device. The movable core member is operatively connected for pivotal movement with and pivotal movement with respect to each rack so as to change a relative location of the receptacle with respect to at least one of the first rack and the second rack based on a relative position of the first rack with respect to the second rack.

DETAILED DESCRIPTION

The description and drawings herein illustrate a drying rack. Various modifications and changes can be made in the structures disclosed without departing from the present disclosure. In general, the figures of an exemplary drying rack are not to scale. It will also be appreciated that the various identified components of the drying rack disclosed herein are merely terms of art that may vary from one manufacturer to another and should not be deemed to limit the present disclosure.

Figure 1:
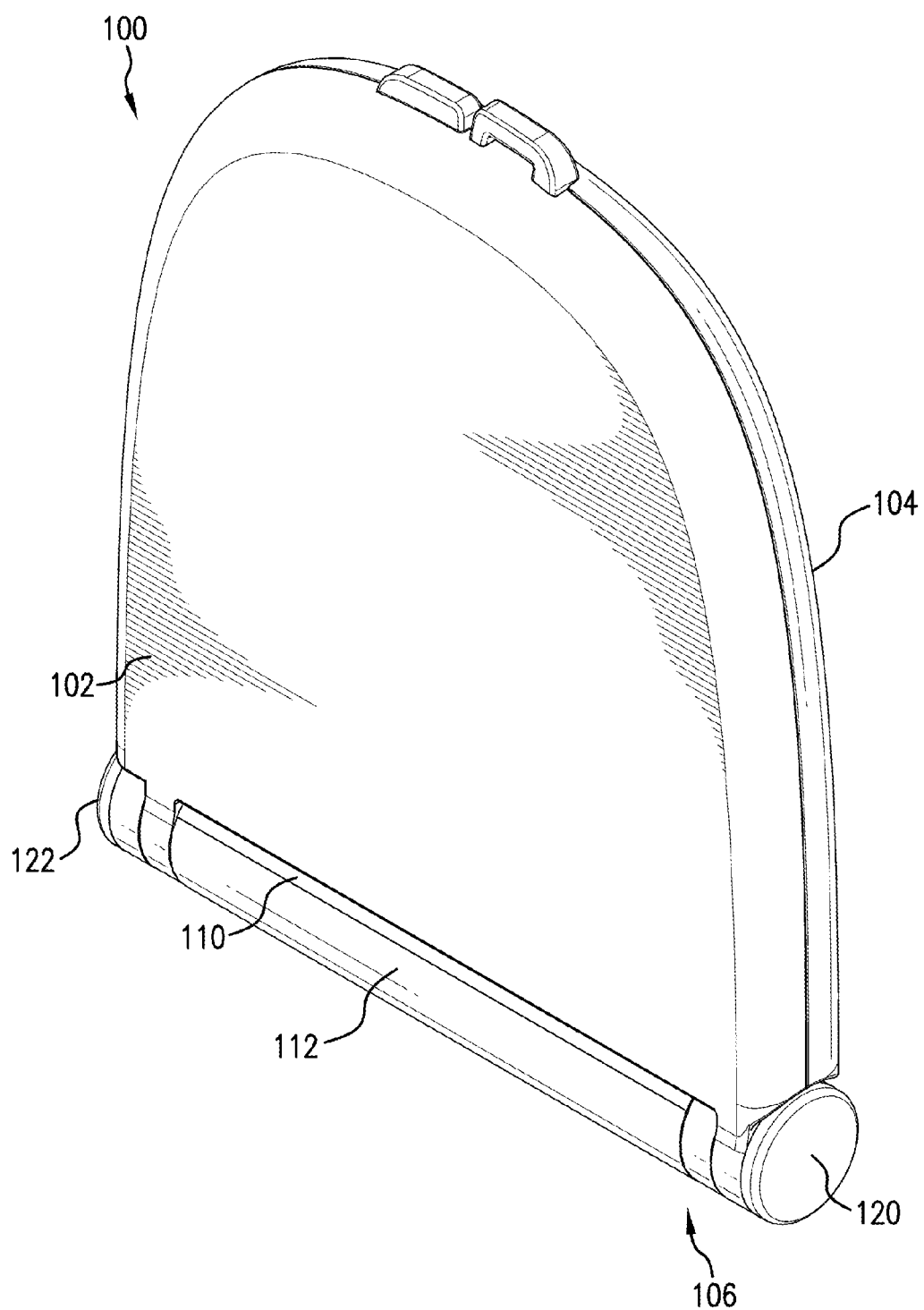
FIG. 1 is a perspective view of a drying rack in a closed position.
Figure 2:
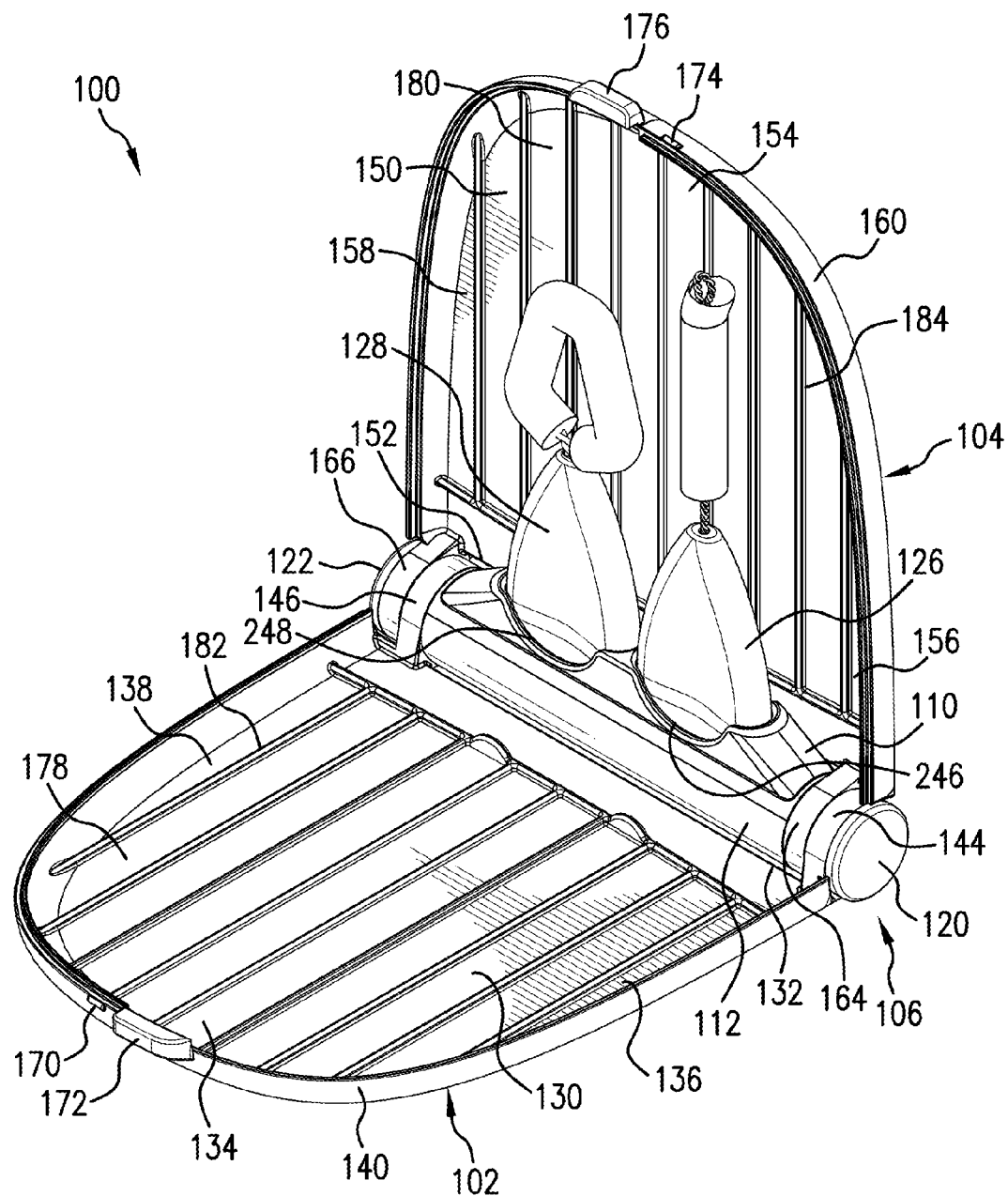
FIG. 2 is a perspective view of the drying rack of FIG. 1 in an open position.
Figure 3:
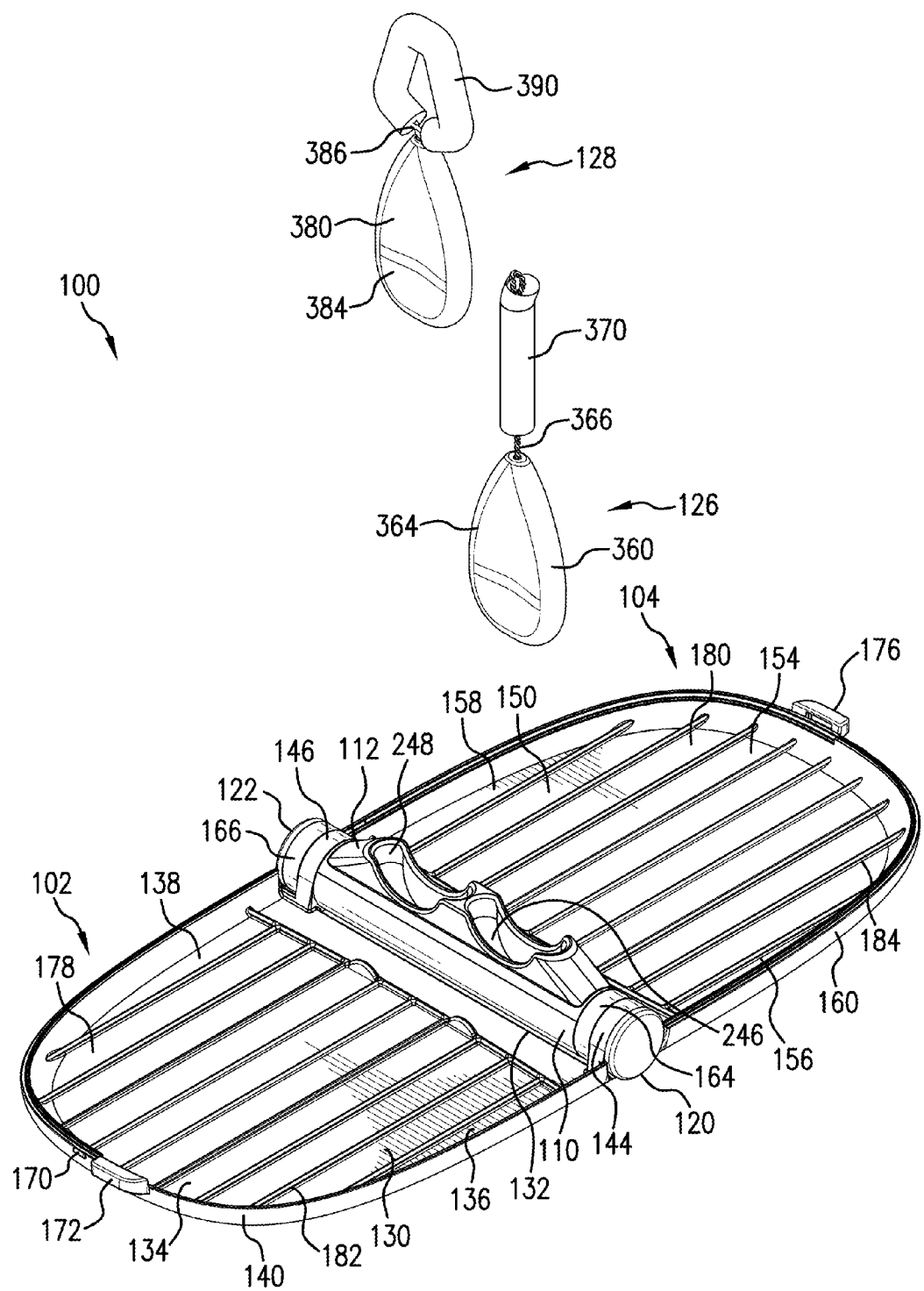
FIG. 3 is a perspective view of the drying rack of FIG. 1 in an open use position with cleaning devices removed from the drying rack.

Referring now to the drawings, wherein like numerals refer to like parts throughout the several views, FIGS. 1-4 illustrate an exemplary drying rack 100 according to the present disclosure for use with, for example, an associated part of a breast pump, such as a breast receiving cup or funnel (not shown). In general, the drying rack 100 includes a first rack 102 and a second rack 104 pivotally connected with the first rack 102 via a hinge assembly 106, which allows the drying rack 100 to occupy a closed position (FIG. 1), an open position (an example of which being shown in FIG. 2) and an open use position (FIG. 3). The hinge assembly 106 includes a movable core member 110 received in a core member housing 112 and connected to the first and second racks 102, 104 by first and second plugs 120, 122. Each of the movable core member 110 and the core member housing 112 can remain substantially stationary as the first rack 102 and the second rack 104 rotate with respect to one another. However, the movable core member 110 and the core member housing 112 can also rotate with either the first rack 102 or the second rack 104 as the first rack 102 and the second rack 104 rotate with respect to one another. The movable core member 110 is configured to releasably hold therein at least one cleaning device, and according to the depicted embodiment, the movable core member releasably holds first and second cleaning devices 126, 128, which is the illustrated embodiment are brushes.

As depicted, the first rack 102 includes a body 130 having a first rack proximal end portion 132, a first rack distal end portion 134 and opposite first and second side portions 136, 138. As shown, the first rack distal end portion 134 can be arc-shaped or curved; although, this is not required. A flange 140 extends outwardly from the body 130 continuously along the first rack distal end portion 134 and each side portion 136, 138. First and second rims or hoops 144, 146 extend from the first rack proximal end portion 132. The first hoop 144 is located at an intersection of the first rack proximal end portion 132 and first side portion 136 and the second hoop 146 is located at the first rack proximal end portion 132 and slightly offset inwardly from the flange 140 at the second side portion 138.

Similarly, the second rack 104 includes a body 150 having a second rack proximal end portion 152, a second rack distal end portion 154 and opposite first and second side portions 156, 158. As shown, the second rack distal end portion 154 can be arc-shaped or curved; although, this is not required. A flange 160 extends outwardly from the body 150 continuously along the second rack distal end portion 154 and each side portion 156, 158. The second rack proximal end portion 152 has first and second rims or hoops 164, 166 extending therefrom. The first hoop 164 is located at the second rack proximal end portion 152 and adjacent, although slightly offset from, the flange 160 at the first side portion 136. The second hoop 166 is located at an intersection of the second rack proximal end portion 152 and the second side portion 158.

When the drying rack 100 is in the closed position, which is shown in FIG. 1, the first and second racks 102, 104 can be releasably connected to each other. To this end, in the depicted embodiment, the first rack 102 includes a tab 170 and a lock member 172 at the first rack distal end portion 134, and the second rack 104 includes a similarly shaped tab 174 and lock member 176 at the second rack distal end portion 154. The lock members 172, 176 are adapted to releasably engage the corresponding tabs 170, 174 in the closed position of the of the drying rack 100, which is when a first item support surface 178 of the first rack 102 faces a second item support surface 180 of the second rack 104. The item support surfaces 178, 180 of the first and second racks 102, 104 define drying surfaces for a breast receiving cup or funnel (as well as other items). Each respective body 130, 150 can be provided with a plurality of ribs 182, 184 which add strength and rigidity of the body and facilitate in the air drying of, for example, a breast receiving cup or funnel seated atop the body 130, 150.

As depicted, the second hoop 146 of the first rack 102 is offset inwardly from the second side portion 138 a greater distance than an offset of the first hoop 144 from the first side portion 136. However, a reverse arrangement is provided on the second rack 104. Particularly, the first hoop 164 of the second rack 104 is offset inwardly from the first side portion 156 a greater distance than an offset of the second hoop 166 from the second side portion 158. With this spatial arrangement of the respective first and second hoops of the first and second racks 102, 104, in the assembled condition of the drying rack 100, the first hoop 144 of the first rack 102 is outward and adjacent to the first hoop 164 of the second rack 104 and the second hoop 166 of the second rack 104 is outward and adjacent to the second hoop 146 of the first rack 102.

Figure 4:
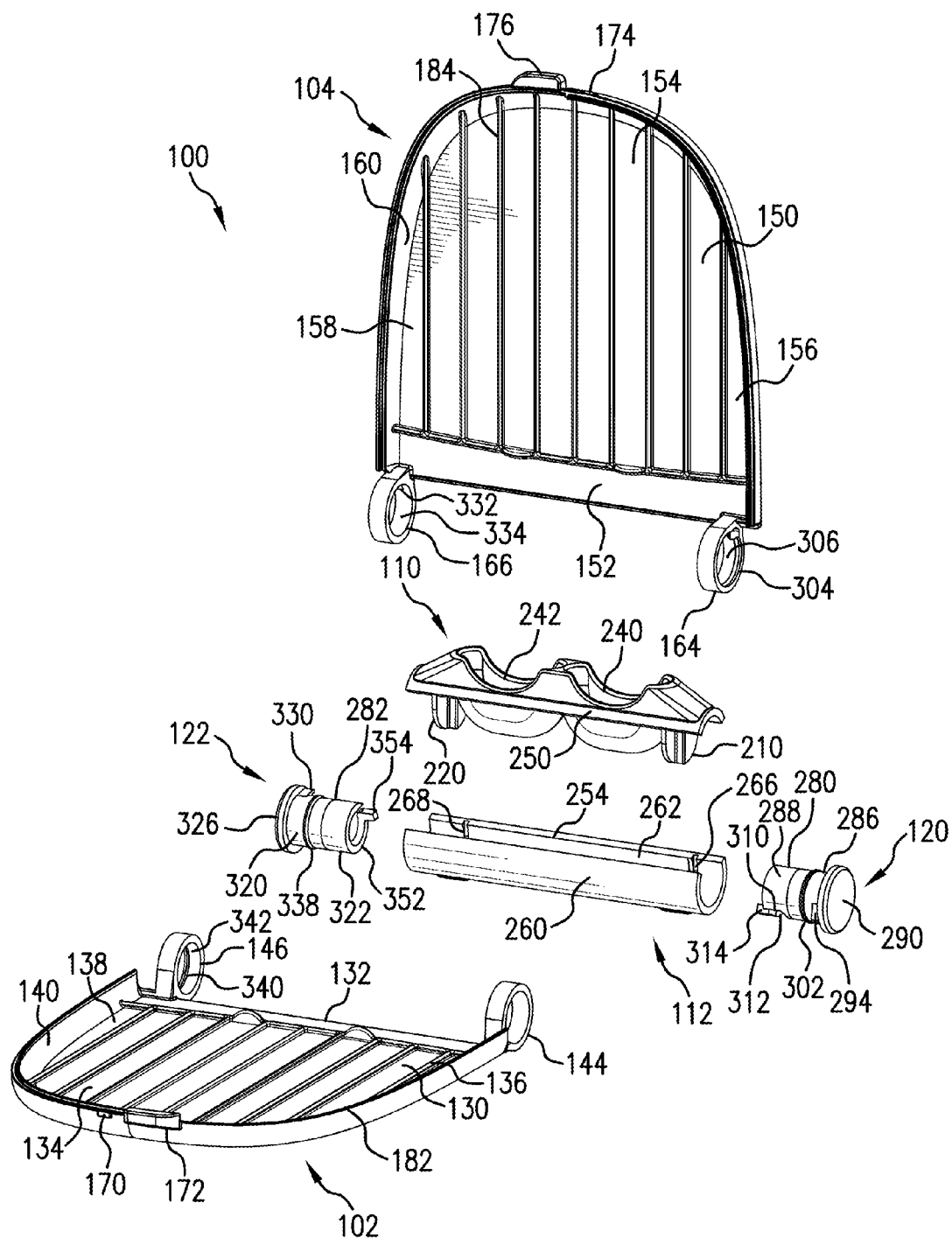
FIG. 4 is an exploded perspective view of the drying rack of FIG. 2 without cleaning devices shown in FIGS. 2 and 3.
Figure 7:
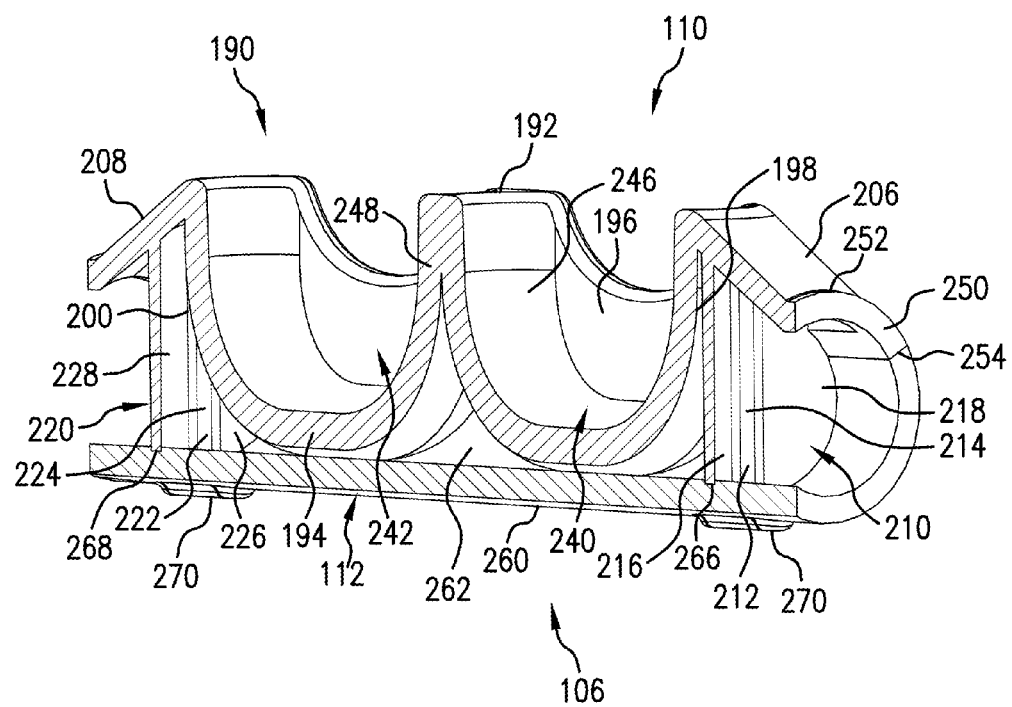
FIGS. 7 and 8 are perspective cross-sectional views of a hinge assembly of the drying rack of FIG. 1.
Figure 8:
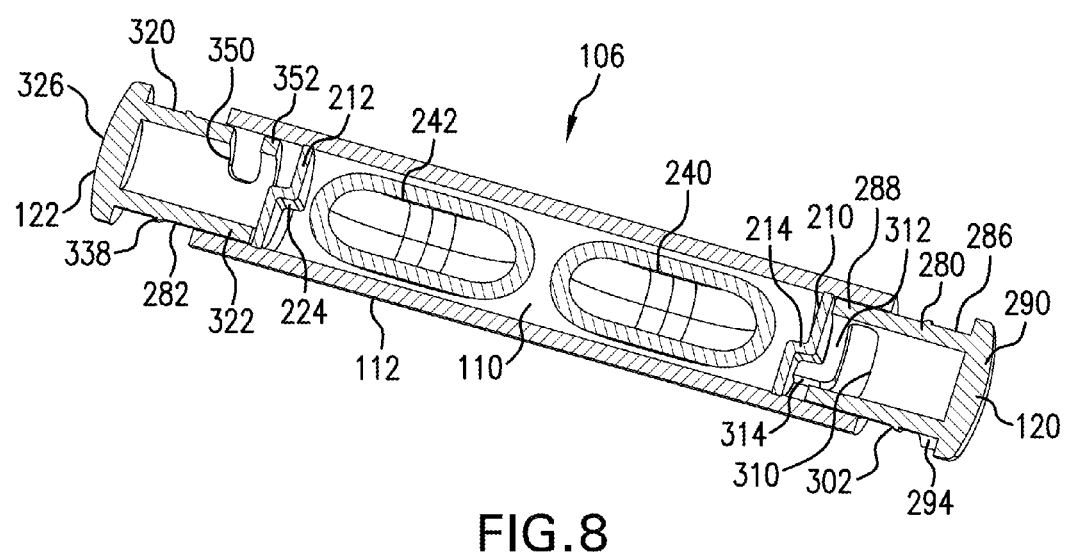

With reference to FIGS. 4 and 7, the movable core member 110 of the hinge assembly 106 includes a body 190 having a base wall 192, first and second side walls 194, 196 depending from the base wall 192, and first and second end walls 198, 200 also depending from the base wall 192. Opposite end portions 206, 208 of the base wall 192 extend outwardly past the first and second end walls 198, 200 and can be canted downwardly toward the core member housing 112. A first tab 210 extends from a lower surface of the base wall 192 and is outwardly adjacent of the first end wall 198. The first tab 210 is provided with a step 212 that defines a ledge 214 extending in a direction transverse to a length direction of the movable core member 110. The step 212 separates the first tab 210 into a first section 216 and a second section 218 which is offset outwardly from the first section. Similarly, a second tab 220 extends from the lower surface of the base wall 192 and is outwardly adjacent of the second end wall 200. The second tab 220 is provided with a step 222 that defines a ledge 224 extending in a direction transverse to the length direction of the movable core member 110. The step 222 separates the second tab 220 into a first section 226 and a second section 228 which is offset outwardly from the first section. As best shown in FIG. 8, the second section 228 of the second tab 220 is opposite to the second section 218 of the first tab 210.

Further, the body 190 of the movable core member 110 has defined therein first and second receptacles 240, 242 dimensioned to releasably secure therein the respective first and second cleaning devices 126, 128. The first and second receptacles 240, 242 are separated by their respective inner walls 246, 248, which are inwardly spaced from the first and second end walls 198, 200. A flange 250 extends about a periphery 252 of the base wall 192 of the body 190 and, as depicted in FIG. 7, is adapted to mate with the an edge surface 254 of the core member housing 112. According to one aspect, the movable core member 110 and the core member housing 112 can be formed as separate components of the hinge assembly 106 that can be assembled mechanically to one another. For example, in assembly the core member housing 112 can be welded or adhered to the movable core member 110. In the illustrated embodiment, the core member housing 112 is generally U-shaped in cross-section and includes an in outer surface 260 and an inner surface 262. The inner surface 262 is provided with first and second grooves 266, 268 dimensioned to receive the respective first and second tabs 210, 220 of the movable core member 110. It should be appreciated that the grooves 266, 268 ensure proper placement of the movable core member 110 within the core member housing 112 and provide a secure engagement between the movable core member 110 and the core member housing 112. According to another aspect, the movable core member 110 and the core member housing 112 of the hinge assembly 106 can be formed as a unitary component, for example, wherein the core member housing 112 is overmolded onto the movable core member 110. Feet 270, which can be formed of an elastomeric material, can be provided on the outer surface of the core member housing 112.

With reference now to FIGS. 4 and 8, each of the first and second plugs 120, 122 includes a respective cylindrical shaped body 280, 282 dimensioned to be received in the core member housing 112. The body 280 of the first plug 120 has a first end portion 286 and a second end portion 288. An enlarged head 290 is located at the first end portion 286 and defines a stop for the insertion of the first plug 120 into the core member housing 112. Located adjacent the head 290 is a radially extending projection 294 dimensioned to be received in a corresponding notch 296 located on an inner surface 298 of the first hoop 144 of the first rack (FIG. 5), and located inwardly of the projection 294 is an annular ring 302 dimensioned to be received in a corresponding annular groove 304 located on an inner surface 306 of the first hoop 164 of the second rack 104. The engagement between the projection 294 and the first hoop 114 ensures that the first plug 120 rotates together with the first rack 102, and the engagement between the ring 302 and the first hoop 164 prevents axial movement of the first plug 120 within the core member housing 112. The second end portion 288 of the body 280 of the first plug 120 includes a slot 310 extending at least partially about a circumference of the body 280. The slot 310 at least partially defines a resilient arm 312 at the second end portion 288, the arm 312 including an axially extending finger 314. It should be appreciated that rotation of the first plug 120 with the first rack 102 causes the finger 314 to contact the ledge 214 provided on the first tab 210 of the movable core member 110 at each of the closed and opened positions of the first rack 102, and the ledge serves as a stop for preventing over-rotation of the first rack 102 with respect to the movable core member 110. However, it should also be appreciated that if a user attempts to over-rotate the first rack 102 beyond its fully opened position, e.g., rotate the first rack 102 in an opening direction beyond the open use position of the drying rack 100 shown in FIG. 3, the flexing of the arm 312 allows the finger 314 to move slightly past the ledge 214 onto the second section 218 of the first tab 210, thereby preventing damage to the drying rack 100.

Figure 5:
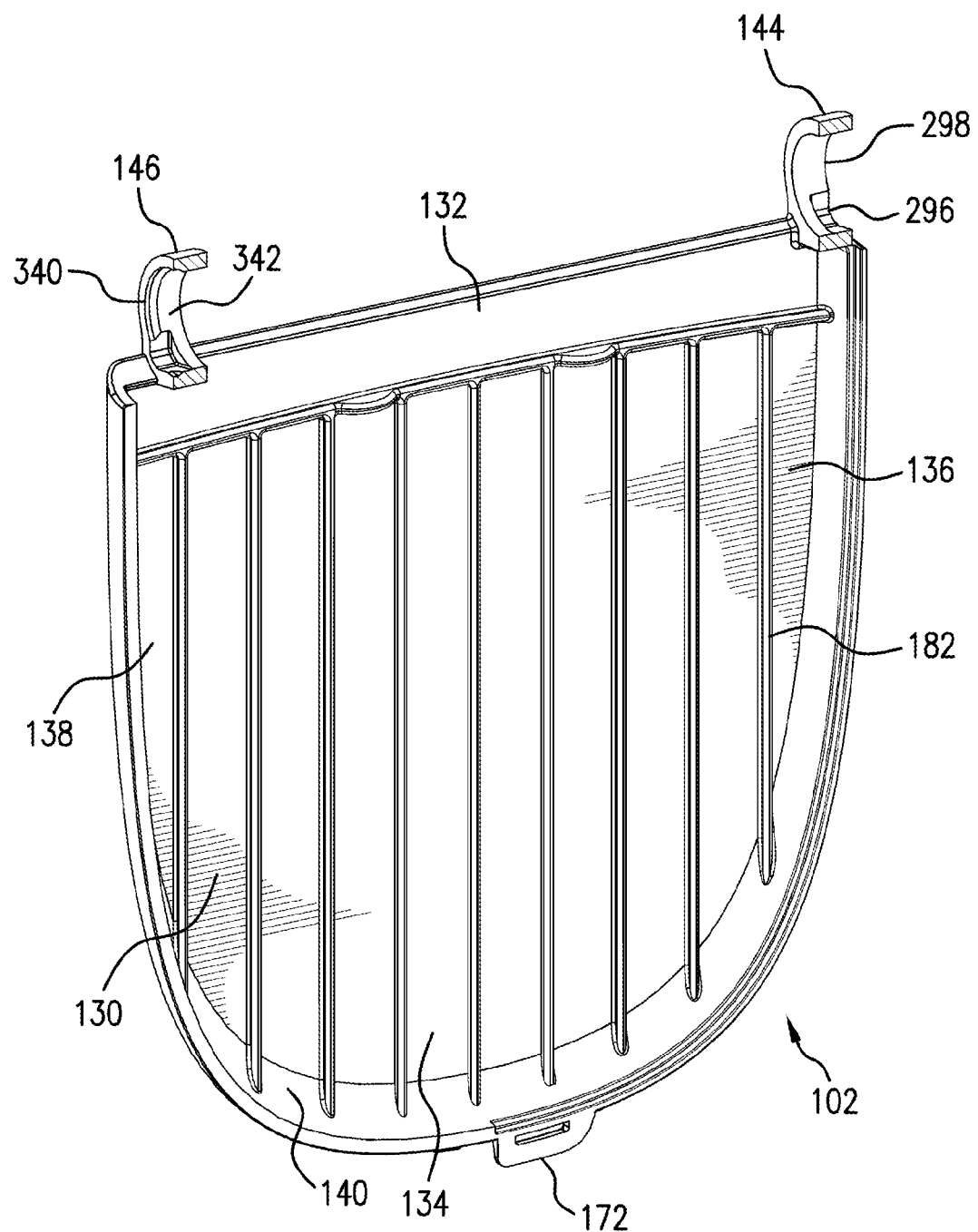
FIG. 5 is a perspective cross-sectional view of one rack of the drying rack of FIG. 1.

Similarly, and with continued reference to FIGS. 4 and 8, the body 282 of the second plug 122 has a first end portion 320 and a second end portion 322. An enlarged head 326 is located at the first end portion 320 and defines a stop for the insertion of the second plug 122 into the core member housing 112. Located adjacent the head 326 is a radially extending projection 330 dimensioned to be received in a corresponding notch 332 located on an inner surface 334 of the second hoop 166 of the second rack (FIG. 4), and located inwardly of the projection 330 is an annular ring 338 dimensioned to be received in a corresponding annular groove 340 located on an inner surface 342 of the second hoop 146 of the first rack 102 (FIG. 5). The engagement between the projection 330 and the second hoop 166 ensures that the second plug 122 rotates together with the second rack 104, and the engagement between the ring 338 and the second hoop 146 prevents axial movement of the second plug 122 within the core member housing 112. The second end portion 322 of the body 282 of the second plug 122 includes a slot 350 extending at least partially about a circumference of the body 282. The slot 350 at least partially defines a resilient arm 352 at the second end portion 322, the arm 352 including an axially extending finger 354. Rotation of the second plug 122 with the second rack 104 causes the finger 354 to contact the ledge 224 provided on the second tab 220 of the movable core member 110 at each of the closed and opened positions of the second rack 104, and the ledge serves as a stop for preventing over-rotation of the second rack 104. Again, it should also be appreciated that if a user attempts to over-rotate the second rack 104 beyond its fully opened position, e.g., rotate the second rack 104 in an opening direction beyond the open use position of the drying rack 100 shown in FIG. 3, the flexing of the arm 352 allows the finger 354 to move slightly past the ledge 224 onto the second section 228 of the second tab 220, thereby preventing damage to the drying rack 100.

Figure 6:
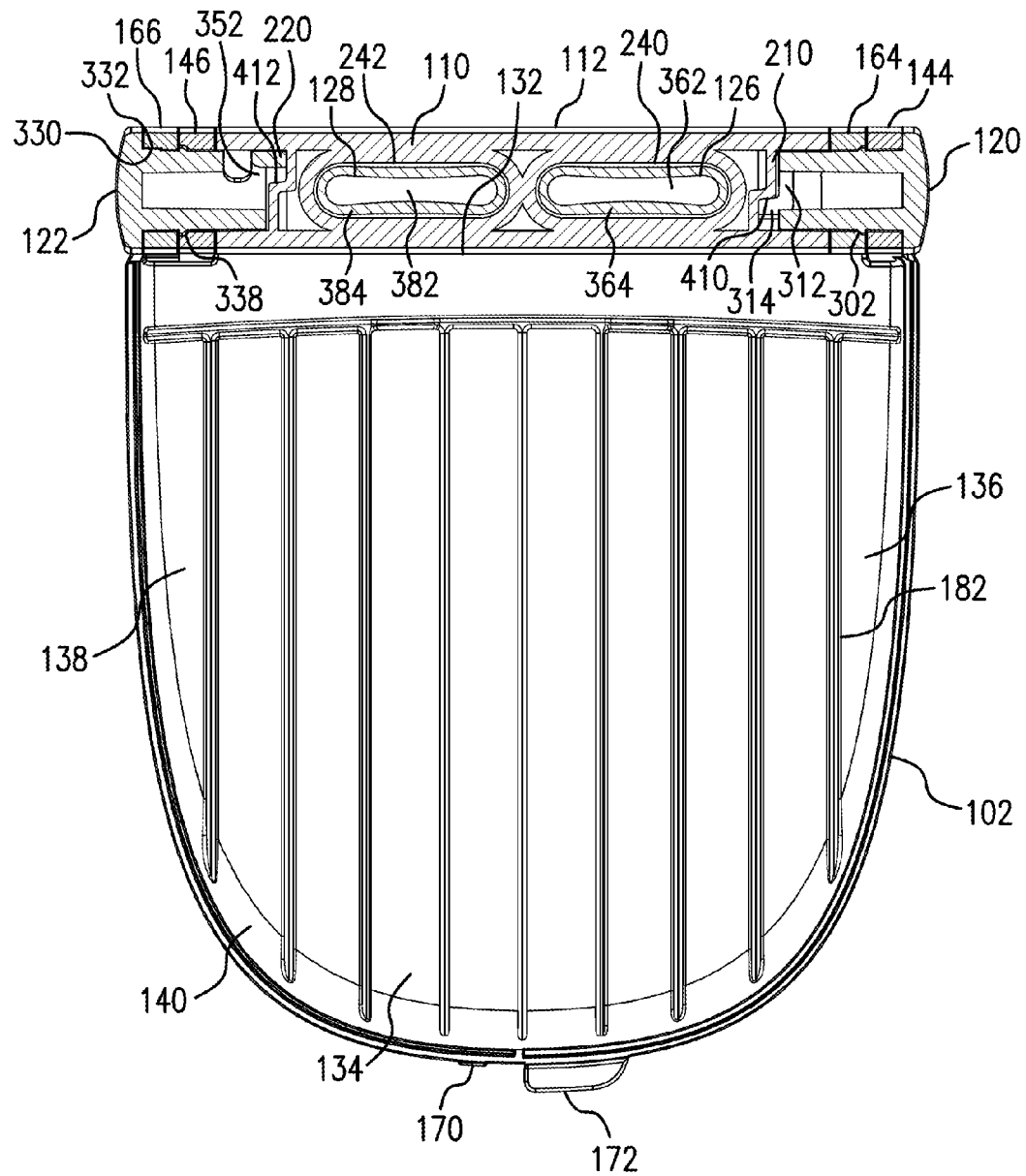
FIG. 6 is a perspective cross-sectional view of the drying rack of FIG. 2.
Figure 9:
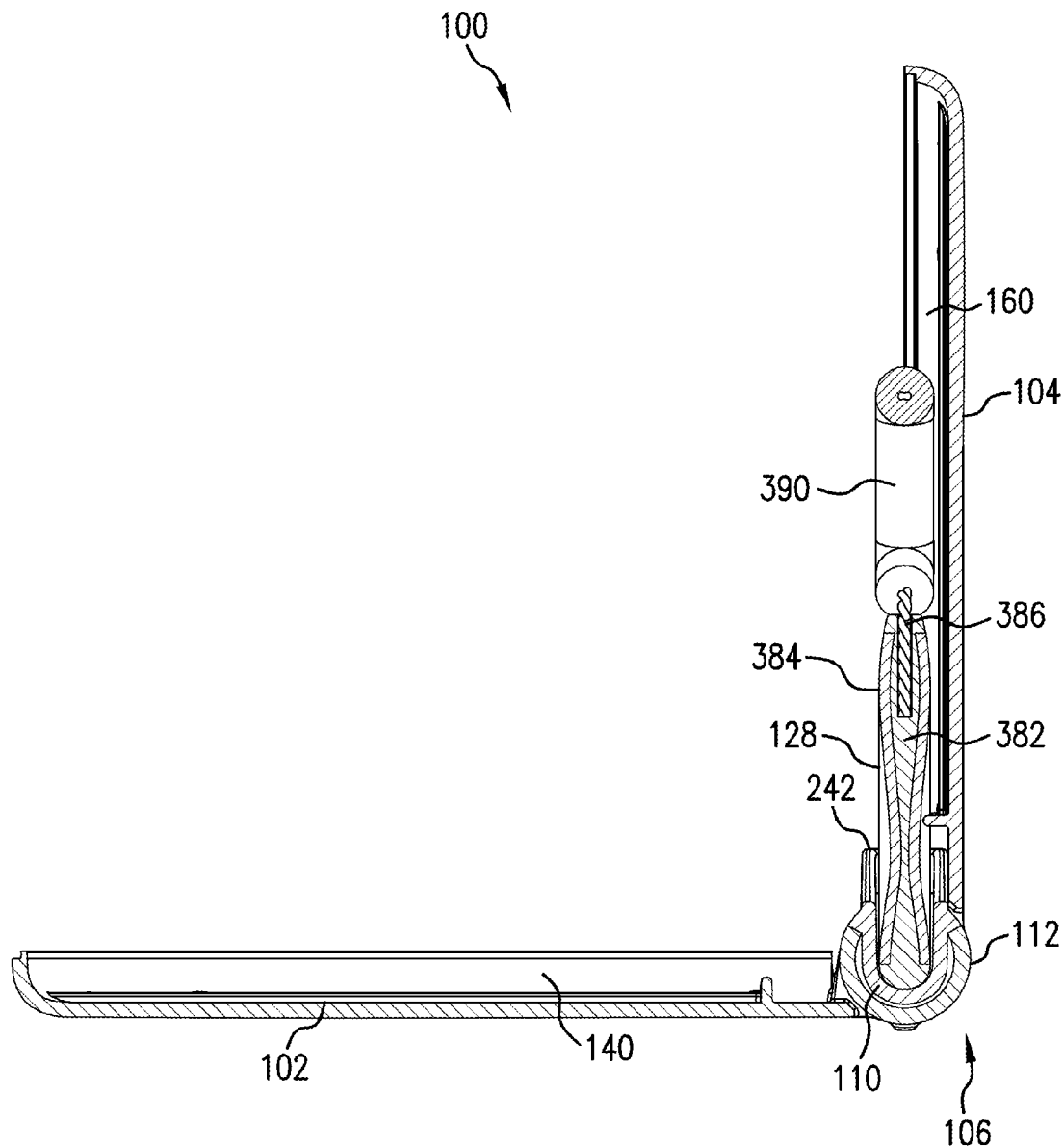
FIG. 9 is another cross-sectional view of the drying rack of FIG. 1.

With reference to FIGS. 3, 6 and 9, the first cleaning device 126 includes a handle 360 which can be defined by a core 362 and an elastomeric outer grip 364 which can be overmold onto the core 362. The handle 360 is dimensioned to be frictionally and releasably received in the first receptacle 240. A wire support 366 has one end portion secured in the core 362. According to one aspect, an elongated cylindrical shaped brush 370 is mounted to the other end portion of the wire support 366. The second cleaning device 128 includes a handle 380 which can be defined by a core 382 and an elastomeric outer grip 384 which can be overmold onto the core 382. The handle 380 is dimensioned to be frictionally and releasably received in the second receptacle 242. A wire support 386 has one end portion secured in the core 382. According to one aspect, an elongated generally triangular shaped brush 390 is mounted to the other end portion of the wire support 386. However, it should be appreciated that the second cleaning device 128 can have a brush similar to the first cleaning device 126.

Figure 10:
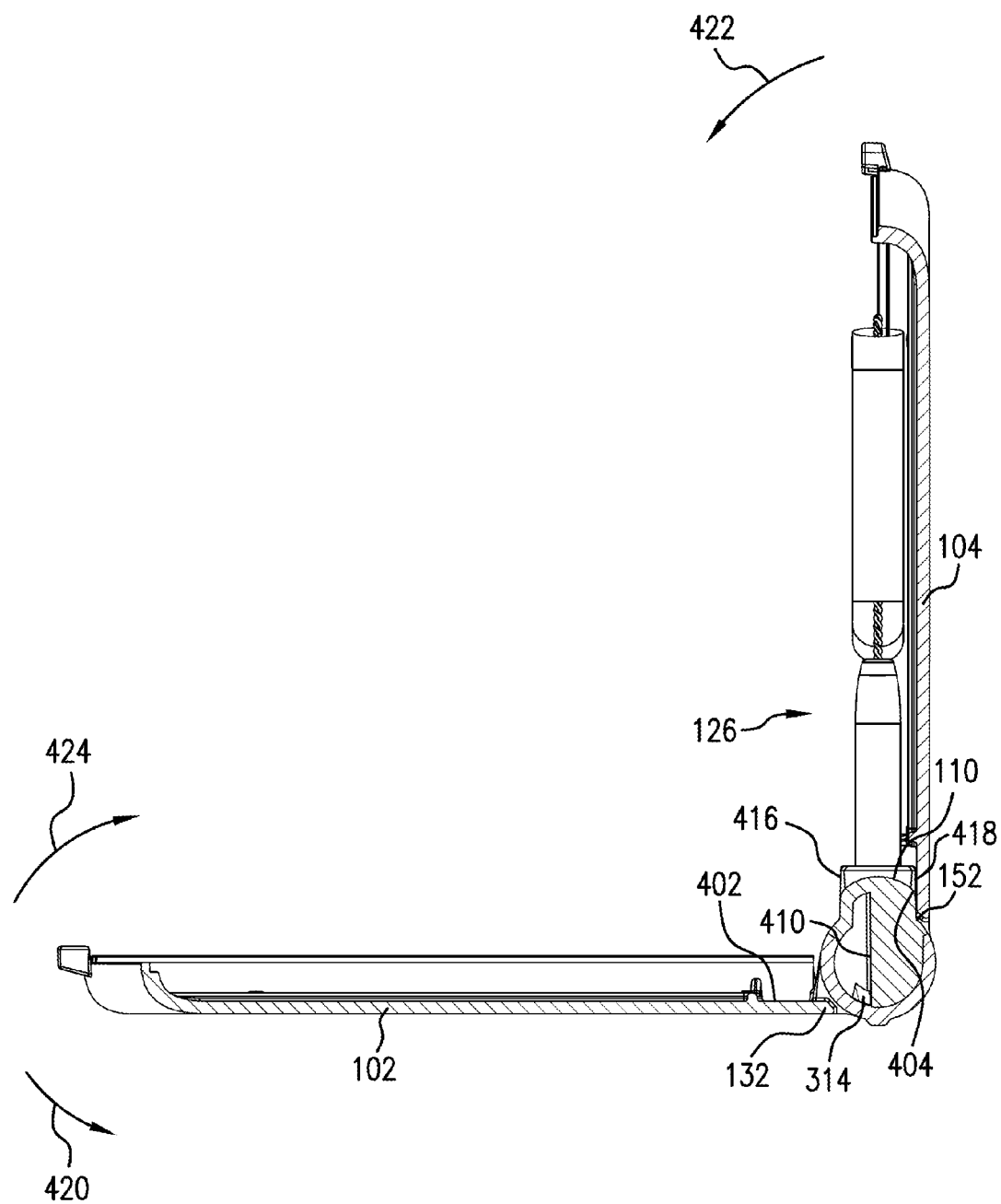
FIG. 10 is another cross-sectional view of the drying rack of FIG. 1.

As described above, the drying rack 100 includes a first rack 102 and a second rack 104 pivotally connected with the first rack 102. The movable core member 110 includes a receptacle (two receptacles 240, 242 are in the illustrated embodiment) each configured to receive an associated cleaning device, such as the cleaning devices 126, 128. The movable core member 110 is operatively connected for pivotal movement with and pivotal movement with respect to each rack 102, 104 so as to change a relative location of the receptacle 240, 242 with respect to at least one of the first rack 102 and the second rack 104 based on a relative position of the first rack 102 with respect to the second rack 104. This allows the cleaning devices 126, 128 to be presented in a vertical orientation when the drying rack 100 is in the open use position, which is shown in FIG. 3. This also allows for a horizontal orientation of the cleaning devices 126, 128, for example when the second rack 104 is brought toward the first rack 102 from the position shown in FIGS. 9 and 10 to the position shown in FIG. 11.

The drying rack 100 includes a contact element provided on or connected with the first rack 102. The contact element can be the finger 314 on the first plug 120, the finger 354 on the second plug 122, a section 402 of the first rack 102 adjacent the first rack proximal end portion 132 or a section 404 of the second rack 104 adjacent the second rack proximal end portion 152. The movable core member 110 includes a contact surface, which can be a surface 410 (FIG. 6) defined by the ledge 214, a surface 412 (FIG. 6) defined by the ledge 224, a surface 416 adjacent the receptacles 240, 242 or a surface 418 adjacent the receptacles 240, 242. The contact elements, i.e., the finger 314 and the section 402, move with the first rack 102 during pivotal movement of the first rack 102 with respect to the second rack 104. The contact elements, i.e., the finger 354 and the section 404, move with the second rack 104 during pivotal movement of the second rack 104 with respect to the first rack 102.

The contact elements, i.e., the finger 314 and the section 402 in the illustrated embodiment, are configured to contact the appropriate contact surface 410 or 416 to rotate the movable core member 110 along with the first rack 102 during at least a portion of the pivotal movement of the first rack 102 with respect to the second rack 104. For example, if the first rack 102 in the position shown in FIG. 10 was rotated in an opening direction, i.e., in the direction of arrow 420, the finger 314 would contact the contact surface 410 defined by the ledge 214 on the movable core member 110 to rotate the movable core member 110 with respect to the second rack 104 in the opening direction. Also, if the second rack 104 in the position shown in FIG. 10 was rotated in a closing direction, i.e., in the direction of arrow 422, the section 404 of the second rack 104 adjacent the second rack proximal end portion 152 would contact the surface 418 on the movable core member 110 to rotate the movable core member 110 with respect to the first rack 102 in the closing direction.

The contact elements, e.g., the finger 314 and the section 402 associated with the first rack 102 in the illustrated embodiment, are spaced from the respective contact surfaces 410 and 416 so as not to contact the contact surfaces 410 and 416 during at least a portion of the pivotal movement of the first rack 102 with respect to the second rack 104. For example, if the first rack 102 in the position shown in FIG. 10 was rotated in a closing direction, i.e., in the direction of arrow 424, the finger 314 would not contact the contact surface 410 defined by the ledge 214 and the section 402 would not contact the contact surface 416 until the first rack 102 contacts the second rack 104. As such, movement of the first rack 102 with respect to the movable core member 110 is also allowed.

Figure 11:
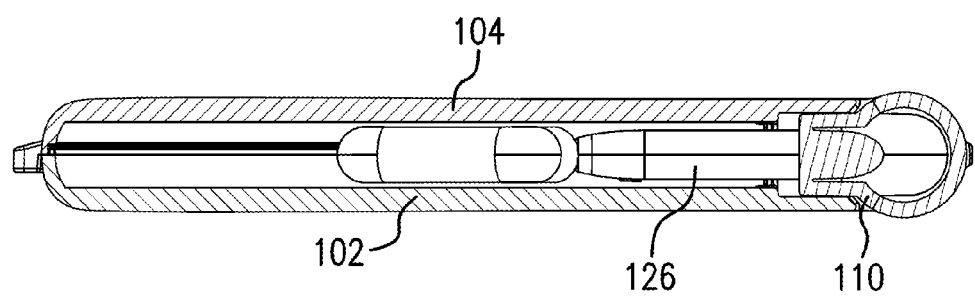
FIG. 11 is a cross-sectional view of the drying rack in the closed position resting on a horizontal support surface.

With reference to FIG. 1, when the drying rack 100 is in the closed position, the first item support surface 178 (FIG. 2) faces the second item support surface 180 (FIG. 2). With reference to FIG. 3, when in the drying rack 100 is in the open use position the first item support surface 178 and the second item support surface 180 are oriented to support associated items to be dried. The movable core member 110 occupies an upright position when the drying rack 100 is in the open use position. When the movable core member 110 is in the upright position shown in FIG. 3, the receptacles 240, 242 are oriented to maintain the cleaning devices 126, 128 so that a longest dimension of each cleaning device 126, 128 is transverse (e.g., perpendicular) to the item support surfaces 178, 180. The movable core member 110 is rotatable to a storage position, which is shown in FIG. 11, rotationally offset (90 degrees in the illustrated embodiment) from the upright position. With reference to FIG. 11, angular movement of the second rack 104 with respect to the first rack 102 beyond a first predetermined angle, which is 90 degrees in the illustrated embodiment, in an opening direction, which would be in the direction of arrow 424 in FIG. 10, from the closed position toward the open use position (shown in FIG. 3) results in rotational movement of the movable core member 110 with respect to the first rack 102. However, angular movement of the second rack 104 with respect to the first rack 102 up to the first predetermined angle in the opening direction may not result in rotational movement of the movable core member 110 with respect to the first rack 102. In other words, angular movement of the second rack 104 with respect to the first rack 102 in the opening direction for the first 90 degrees may not result in rotational movement of the movable core member 110 with respect to the first rack 102.

It will be appreciated that various of the above-disclosed and other features and functions, or alternatives thereof, may be desirably combined into many other different systems or applications. By way of example, the exemplary drying rack was herein described for use with associated parts of a breast pump. However, it should be appreciated that the exemplary drying rack is not limited to that particular use and that alternative uses for the drying rack are contemplated. Also that various presently unforeseen or unanticipated alternatives, modifications, variations or improvements therein may be subsequently made by those skilled in the art which are also intended to be encompassed by the following claims.

What is claimed is:

1. A drying rack comprising:
a first rack;
a second rack pivotally connected with the first rack;
a movable core member having a receptacle configured to receive an associated cleaning device, wherein the movable core member is operatively connected for pivotal movement with and pivotal movement with respect to each rack so as to change a relative location of the receptacle with respect to at least one of the first rack and the second rack based on a relative position of the first rack with respect to the second rack;
a contact element provided on or connected with the first rack, wherein the movable core member includes a contact surface, wherein the contact element moves with the first rack during pivotal movement of the first rack with respect to the second rack, wherein the contact element is spaced from the contact surface so as not to contact the contact surface during at least a portion of the pivotal movement of the first rack with respect to the second rack; and
a first plug connected to the first rack and the movable core member, wherein the first plug rotates along with the first rack as the first rack pivots with respect to the second rack and the contact element is provided on the first plug,
wherein the first rack includes a first item support surface, a first rack distal end portion and a first rack proximal end portion, and the second rack includes a second item support surface, a second rack distal end portion and a second rack proximal end portion; and
wherein the drying rack is positionable in a closed position and an open use position, when in the closed position the first item support surface faces the second item support surface, and when in the open use position the first item support surface and the second item support surface are oriented to support associated items to be dried,
wherein the movable core member occupies an upright position when the drying rack is in the open use position,
wherein the movable core member is rotatable with each rack to a storage position rotationally offset from the upright position.

2. The drying rack of claim 1, wherein the contact element is configured to contact the contact surface to rotate the movable core member along with the first rack during at least a portion of the pivotal movement of the first rack with respect to the second rack.

3. The drying rack of claim 1, further comprising a second plug connected to the second rack and the movable core member, wherein the second plug rotates along with the second rack as the second rack pivots with respect to the first rack, wherein the contact element is a first contact element provided on the first plug and the drying rack further includes a second contact element provided on the second plug.

4. The drying rack of claim 1, wherein the first rack includes a first hoop that receives the first plug, wherein the first plug engages with the first hoop so that the first plug rotates together with the first rack.

5. The drying rack of claim 1, further comprising a second plug connected to the second rack and the movable core member, wherein the second plug rotates along with the second rack as the second rack pivots with respect to the first rack, wherein the contact element is a first contact element provided on the first plug and the drying rack further includes a second contact element provided on the second plug, wherein the first rack includes a first hoop that receives the first plug, wherein the first plug engages with the first hoop so that the first plug rotates together with the first rack, and wherein the second rack includes a second hoop that receives the second plug, wherein the second plug engages with the second hoop so that the second plug rotates together with the second rack.

6. The drying rack of claim 1, wherein the first plug includes a resilient arm and the contact element is provided on the resilient arm.

7. The drying rack of claim 6, wherein the resilient arm allows the contact element to ride over the contact surface when the first rack is moved in an opening direction beyond the open use position.

8. The drying rack of claim 1, wherein the first rack proximal end portion is adjacent the movable core member, and the contact element is provided adjacent the first rack proximal end portion and the contact surface is a portion of the movable core member adjacent the receptacle.

9. The drying rack of claim 1, wherein the first rack, the second rack and the movable core member are configured such that angular movement of the first rack with respect to the second rack beyond a first predetermined angle in an opening direction from the closed position toward the open use position results in rotational movement of the movable core member with respect to the second rack.

10. The drying rack of claim 9, wherein the first rack, the second rack and the movable core member are configured such that angular movement of the first rack with respect to the second rack up to the first predetermined angle in the opening direction does not result in rotational movement of the movable core member with respect to the second rack.

11. The drying rack of claim 10, wherein the first predetermined angle is 90 degrees.

12. The drying rack of claim 1, wherein the first rack, the second rack and the movable core member are configured such that when the drying rack is in the open use position with each rack resting on a horizontal support surface, the movable core member is oriented in an upright configuration.

13. The drying rack of claim 1, wherein the first rack, the second rack and the movable core member are configured such that when the drying rack is in the closed position with the second rack resting on a horizontal support surface and the first rack resting on the second rack, the movable core member is oriented in a storage configuration.

* * * * *